(12) United States Patent
Bird et al.

(10) Patent No.: US 6,818,622 B2
(45) Date of Patent: Nov. 16, 2004

(54) SELECTIVE MMP INHIBITORS HAVING REDUCED SIDE-EFFECTS

(75) Inventors: John Bird, Cambridge (GB); John Gary Montana, Cambridge (GB); Ruth Elizabeth Wills, Cambridge (GB); Andrew Douglas Baxter, Cambridge (GB); David Alan Owen, Cambridge (GB)

(73) Assignee: Darwin Discovery Ltd. (GB)

( * ) Notice: Subject to any disclaimer, the term of this patent is extended or adjusted under 35 U.S.C. 154(b) by 289 days.

(21) Appl. No.: 09/862,035

(22) Filed: May 21, 2001

(65) Prior Publication Data

US 2002/0035065 A1 Mar. 21, 2002

Related U.S. Application Data

(63) Continuation of application No. 09/034,080, filed on Mar. 3, 1998, now abandoned.

(30) Foreign Application Priority Data

Mar. 3, 1997 (GB) ............................................. 9704350
Feb. 6, 1998 (GB) ............................................. 9802622

(51) Int. Cl.$^7$ ............................................... A61K 38/00
(52) U.S. Cl. ................................ 514/19; 514/2; 514/6; 530/868; 260/998.2; 260/998.21
(58) Field of Search ................ 514/19, 2, 6; 260/998.2, 260/998.21; 530/868

(56) References Cited

PUBLICATIONS

Solorzano et al., The Journal of Immunology, vol. 158, pp. 414–419, 1997.*

\* cited by examiner

*Primary Examiner*—Jon P. Weber
*Assistant Examiner*—Abdel A. Mohamed
(74) *Attorney, Agent, or Firm*—Saliwanchik, Lloyd & Saliwanchik

(57) ABSTRACT

The subject invention pertains to matrix metalloproteinase (MMP) inhibitors that exhibit an $IC_{50}$ of below $10^{-4}$M against MMP and have substantially no activity against non-MMP metalloproteinase-related events. The MMP inhibitors of the invention have reduced side-effects, especially with respect to joint pain.

3 Claims, No Drawings

SELECTIVE MMP INHIBITORS HAVING REDUCED SIDE-EFFECTS

CROSS-REFERENCE TO RELATED APPLICATION

This application is a continuation of U.S. application Ser. No. 09/034,080 filed Mar. 3, 1998, now abandoned.

FIELD OF THE INVENTION

This invention relates to selective MMP inhibitors having reduced side-effects.

BACKGROUND OF THE INVENTION

Compounds having the ability to inhibit matrix metalloproteinases (MMPs) and optionally also TNFα release are described in WO-A-9513289, WO-A-9611209, WO-A-9635711, WO-A-9635712, WO-A-9635714, WO-A-9635687, WO-A-9712902, WO-A-9719075, WO-A-973 8007, WO-A-9805635 and WO-A-9806696. All these specifications are incorporated herein by reference. By way of example, WO-A-9611209 (Examples 52 and 72) and WO-A-9712902 (Example 6) disclose (S)-N-[2-mercapto-5-phthalimido]pentanoyl-L-leucyl-(S)-tert-leucine N-methylamide, 2S-[4-(2,5-dioxopyrrolidin-1-yl)-2-mercaptobutyrylamino]-4-methylpentanoic acid (2,2-dimethyl-1S-methylcarbamoylpropyl)amide, and 2-[2-mercapto-4-(3,4,4-trimethyl-2,5-dioxoimidazolidin-1-yl) butyrylamino]-4-methylpentanoic acid (2,2-dimethyl-1-methylcarbamoylpropyl)amide, as racemates. Other compounds of this general type are also known.

MMPs are a group of structurally related endopeptidases that degrade the proteinaceous elements of the extracellular matrix. A number of important features are shared by members of the MMP family and include a zinc atom at the catalytic active site, catalytic activity at neutral pH, initial existence as inactive proenzymes, activation involving removal of an N-terminal domain, structural stabilisation by calcium, and inhibition of the catalytically active forms by a family of specific protein inhibitors called Tissue Inhibitor of Metalloproteinases (TIMPs). The MMP family currently consists of twenty members including MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19 and MMP-20 ("classical MMPs").

The MMPs are a sub-family of a much larger group of zinc-containing proteinases which include the Reprolysins and Serralysins, and the Astacin family. Of particular interest are the Adamalysins, members of the Reprolysin family, which include the metalloproteinase involved in the release of TNFα and which is presumably inhibited by compounds such as those described in the patent publications/applications identified above.

It has been demonstrated that compounds which inhibit MMPs also have the capability to inhibit a number of other events that are mediated by metalloproteinases and that include the release of TNFα, CSF-1, TGFα, L-selectin, CD30 and Fas Ligand and the shedding of the IL-6, TNF-RI and TNF-RII receptors. See Hooper et al (1997), Biochem. J., 321:265–279.

MMP inhibitors have been proposed for use in patients with arthritis conditions especially where degradation of cartilage occurs, a process known to involve MMPs. In addition, the use of these compounds in the treatment of various cancers has been advocated. Inhibition of the MMPs, which have been associated with certain disease modalities, offers potential therapeutic benefit. However, the inhibition of other non-MMP metalloproteinases may offer no therapeutic benefit and indeed could be deleterious. For example, it has been suggested that MMP inhibitors which also inhibit the release of TNFα may have a role in exacerbating liver injury; see Solorzano et al (1997), J. Immunol., 158:414–419.

Similarly, early clinical evidence from the use of MMP inhibitors suggests that their use is associated, in many patients, with joint pain. See Wojtowicz-Praga et al, Lombardi Cancer Center, Georgetown University Hospital, Washington D.C. & BBL Anapolis Md., Am. Soc. Clin. Oncol. (May 1996) "The Pharmacokinetics (PK) of Marimastat (BB-2516), A Novel Matrix Metalloproteinase Inhibitor (MMPI) administered orally to patients with metastatic lung cancer". The problem may require treatment "holidays", for up to 50% of the course of treatment, or the administration of non-steroidal anti-inflammatory agents (NSAIDs).

SUMMARY OF THE INVENTION

This invention is based on the appreciation that compounds having particularly valuable properties are of the type which have activity against the classical MMPs, but lack or have little activity against non-MMP metalloproteinase (MP)-related events. This particular profile of activity may confer a therapeutic benefit, particularly regarding the joint pain and tendonitis seen with less selective compounds. Treatment "holidays" may be avoided, e.g. allowing continued treatment. The use of NSAIDs can also be avoided.

This selectivity may be defined in terms of a specific range of activity in defined models of MMP and MP effects. In particular, compounds to which this invention relates have characteristics x and y wherein:

x=MMP inhibition, in terms of $IC_{50}$ measured as described in Example A below; and y=Inhibition of MP-related effects, in terms of $IC_{50}$ as described in Examples B–F below;

x is below $10^{-4}$ M, preferably below $10^{-6}$ M, more preferably $10^{-6}$ M to $10^{-9}$ M or $10^{-10}$ M; and y is greater than $10^{-7}$ M, preferably greater than $10^{-6}$ M, more preferably $10^{-6}$ M to $10^{-4}$ M.

An important characteristic related to y is that y is greater or equal to $2\times10^{-5}$ for at least 4 out of 5 MP-related effects defined by Examples B–F; this is distinct from most prior art compounds having characteristic x.

DESCRIPTION OF THE INVENTION

It has become clear that MMP inhibitors that are very effective in certain areas, e.g. as anti-cancer agents, may have undesirable side-effects. In particular, it appears that, by attaining the selectivity described above, compounds of this invention may overcome the known problems of joint pain experienced by a proportion, albeit significant (c. 30%), of patients treated with MMP inhibitors. The selectivity may be determined by the use of an appropriate assay, for example as described in Examples A–F.

Specific examples of compounds showing the desired profile are those of Examples 1 and 2 and cpd. 3 (see below). These three compounds have been tested in the marmoset tendonitis study. This procedure for this study has been defined by Wojtowicz-Praga et al, supra. The study was performed with oral dosing at 30 and 100 mg/kg for 3 months. Repeated plasma sampling showed sustained levels in excess of the enzymes' $IC_{50}$, up to 9 h post-dose.

Continuous clinical observation revealed no adverse effects. Histological observation revealed no adverse effects on joints and tendons. This is not necessarily seen with all MMP inhibitors. See Hooper et al, supra. It indicates that such compounds are suitable for continued administration.

A compound of the invention may be given in a composition, by a route and/or in an amount that is already known for that compound or for analogues thereof, e.g. as described in the patent specifications identified above. It may be given to patients who have already experienced joint pain (under any circumstances) and to those who are susceptible to joint pain, e.g. those having injured joints. It is within the ability of one skilled in the art to determine which patients are at risk from this complication.

The compound may be used in the treatment or prophylaxis of cancer, inflammation or any condition associated with MMP activity. Many examples are given in the patent publications/applications identified above.

The duration of administration may be conducted on a regular basis, without interruption. This may involve periods of at least 1, 2, 3, 6 or more months

EXAMPLE A

MMP Inhibition Activity-Fluorimetric Assay

The potency of inhibitors of collagenase-1 (MMP-1), collagenase-2 (MMP-8), collagenase-3 (MMP-13), gelatinase-A (MMP-2), gelatinase-B (MMP-9) and stromelysin-1 (MMP-3) is determined using the following procedure:

Inhibitors are dissolved in dimethyl sulphoxide containing 0.02% β-mercaptoethanol, and serial dilutions are prepared. Activated enzyme is incubated in assay buffer containing 50 mM Tris, pH 7.4, 5 mM $CaCl_2$, 0.002% $NaN_3$ and Brij 35 in the presence and absence of inhibitor. Samples are preincubated at 37° C. for 15 minutes before the addition of the fluorimetric substrate (Mca-Pro-Leu-Gly-Leu-Dpa-Ala-Arg-$NH_2$) to a final concentration of 10 μM. The assay is incubated for 20–30 min at 37° C. and then read in a Fluoroscan II at $\lambda_{ex}$ (340 nm) and $\lambda_{em}$ (405 nm).

The enzyme activity is compared to activity in a control devoid of inhibitor. Results are reported as that inhibitor concentration effecting 50% inhibition of the enzyme ($IC_{50}$).

EXAMPLE B

Inhibition of TNFα Production

The potency of inhibitors of the production of TNFα is determined using the following procedure:

A 100 μM solution of the inhibitor being tested or dilutions thereof is incubated at 37° C. in an atmosphere of 5% $CO_2$ with peripheral blood mononuclear cells (PBMC). PBMC are isolated from buffy coats by standard procedures using Ficoll. The PBMC are suspended in RPMl 1640 medium with 2% fetal calf serum at a cell density of $2\times10^6$/ml and stimulated with LPS. After 18 hours the supernatant is assayed for the levels of TNFα using a commercially available ELISA kit.

The activity in the presence of 100 μM inhibitor or dilutions thereof is compared to activity in a control devoid of inhibitor. Results are reported as that inhibitor concentration effecting 50% inhibition of the production of TNFα.

EXAMPLE C

Inhibition of L-Selectin Shedding

An assay of L-selectin shedding by peripheral blood mononuclear cells (PBMC) is conducted as follows:

PBMC are isolated from buffy coats by standard procedures using Ficoll. A 100 μM solution of the inhibitor being tested or dilutions thereof is incubated for 20 min at 37° C. in an atmosphere of 5% $CO_2$ with $4\times10^6$/ml PBMC stimulated with PMA. The cells are centrifuged down and the supernatants tested for sL-selectin using a commercially available ELISA kit.

The activity in the presence of 100 μM inhibitor or dilutions thereof is compared to activity in a control devoid of inhibitor. Results are reported as that inhibitor concentration effecting 50% inhibition of the shedding of L-selectin.

EXAMPLE D

Inhibition of sIL-1RII Shedding

An assay of sIL-1RII shedding by PBMC is conducted as follows:

PBMC are isolated from buffy coats by standard procedures using Ficoll. A 100 μM solution of the inhibitor being tested or dilutions thereof are incubated for 18 h at 37° C. in an atmosphere of 5% $CO_2$ with $2\times10^6$/ml PBMC stimulated with IL-13. The cells are centrifuged down and the supernatants tested for sIL-1RII using a commercially available ELISA kit.

The activity in the presence of 100 μM inhibitor or dilutions thereof is compared to activity in a control devoid of inhibitor. Results are reported as that inhibitor concentration effecting 50% inhibition of the shedding of sIL-1RII.

EXAMPLE E

Inhibition of IL-6R Shedding

An assay of sIL-6R shedding by HL-60 cells is conducted as follows:

PBMC are isolated from buffy coats by standard procedures using Ficoll. A 100 μM solution of the inhibitor being tested or dilutions thereof is incubated for 24 h at 37° C. in an atmosphere of 5% $CO_2$ with $2\times10^6$/ml HL-60 cells stimulated with PMA. The cells are centrifuged down and the supernatants tested for sIl-6R using a commercially available ELISA kit.

The activity in the presence of 100 μM inhibitor or dilutions thereof is compared to activity in a control devoid of inhibitor. Results are reported as that inhibitor concentration effecting 50% inhibition of the shedding of IL-6R.

EXAMPLE F

Inhibition of TNF RII Shedding

The potency of inhibitors of the shedding of TNF RII is determined using the following procedure:

A 100 μM solution of the inhibitor being tested or dilutions thereof is incubated at 37° C. in an atmosphere of 5% $CO_2$ with THP-1 cells (human monocytes) suspended in RPMl 1640 medium and 20 μM β-mercaptoethanol at a cell density of $1\times10^6$/ml and stimulated with LPS (lipopolysaccharide). After 18 hours the supernatant is assayed for the levels of sTNF RII using a commercially available ELISA kit.

The activity in the presence of 0.1 mM inhibitor or dilutions thereof is compared to activity in a control devoid of inhibitor. Results are reported as that inhibitor concentration effecting 50% inhibition of the shedding of TNF RII.

The following Intermediates illustrate stages in the synthesis of the compound of Example 1.

Intermediate 1

(S)-(2,2-Dimethyl-5-oxo[1,3]dioxolan-4-yl)acetic Acid (L)-Malic acid (200 g) was added to a mixture of acetone (800 mL) and 2,2-dimethoxypropane (342 mL) with stirring under nitrogen. Montmorillonite K-10 clay (5 g) was added to the solution and stirred for 17 hours, then the solution was filtered and reduced in volume to approximately 450 mL. The solution was cooled to 5° C., and the resultant crystals of the title compound filtered off (108 g, 42%). MP 108–109.5° C.

Intermediate 2

(S)-5-(2-Hydroxyethyl)-2,2-dimethyl[1,3]dioxolan-4-one

Intermediate 1 (50 g) was dissolved in tetrahydrofuran (400 mL) and cooled to 2° C. To this solution was carefully added borane-methyl sulfide complex (45.5 mL) and the mixture was stirred for 63 hours. The mixture was evaporated to a clear oil, dissolved in ethyl acetate (600 mL), washed with saturated aqueous sodium bicarbonate (100 mL) and water (100 mL) and dried over magnesium sulfate. Filtration and evaporation in vacuo afforded the title compound as a clear oil (36 g, 79%).

TLC $R_f$ 0.41 (Ethyl acetate: Hexane, 1:1)

Intermediate 3

(S)-5-(2-Mesyloxyethyl)-2,2-dimethyl[1,3]dioxolan-4-one

Intermediate 2 (24 g) was dissolved in dichloromethane (480 mL) and cooled to 2° C. To this solution was added mesyl chloride (14.5 mL) followed by dropwise addition of triethylamine (25 mL). The solution was then warmed to room temperature and stirred for 40 minutes, washed with water (2×120 mL), brine (60 mL) and dried over magnesium sulfate. Filtration and evaporation in vacuo afforded the title compound as a clear oil (37.4 g, 100%).

TLC $R_f$ 0.48 (Ethyl acetate: Hexane, 1:1)

Intermediate 4

(S)-1-[2-(2,2-Dimethyl-5-oxo[1,3]dioxolan-4-yl)-ethyl]-pyrrolidine2,5-dione

Intermediate 3 (5 g) was dissolved in N,N-dimethylformamide (50 mL) and potassium succinimide (3.7 g) and sodium iodide (0.6 g) added. The mixture was then heated to 70° C. for 15 hours after which time the solvent was removed in vacuo. The residue was dissolved in ethyl acetate (100 mL) and filtered through a plug of silica. The plug of silica was washed with further ethyl acetate (300 mL) and the combined organic solutions evaporated to an oil, which upon trituration with diethyl ether (5 mL) and cooling to 2° C. provided crystals which were filtered to give the title compound (2.4 g, 47%).

TLC: $R_f$ 0.88 (Ethyl acetate Methanol, 8:2, one drop of acetic acid).

Intermediate 5

(S)-4-(2,5-Dioxopyrrolidin-1-yl)-2-hydroxybutyric Acid

Intermediate 4 (2.3 g) was suspended with Dowex 50WX4–400 resin (1.0 g) in methanol (23 mL) and water (4.6 mL) then stirred for 19 hours. The resin was removed by filtration and solvent removed in vacuo to give an oil. The oil was seeded with some crystals of the product and cooled to −25° C., upon complete crystallisation, the solid was washed on a filter bed with diethyl ether (10 mL) and ethyl acetate (1 mL) affording the title compound (1.5 g, 78%).

TLC $R_f$ 0.20 (Ethyl acetate: Methanol, 8:2, one drop of acetic acid).

Intermediate 6

(R)-2-Bromo-4-(2,5-dioxopyrrolidin-1-yl)butyric Acid

Intermediate 5 (18.4 g) was dissolved in 30% hydrobromic acid/acetic acid (111 mL) under nitrogen, and the mixture stirred at ambient temperature for 35 minutes. After this time the reaction was poured into water (300 mL) and extracted with ethyl acetate (4 ×400 mL). The combined extracts were washed with brine (100 mL), dried over magnesium sulfate, filtered and evaporated to an oil. This was then purified on silica (450 g) with an eluent of dichloromethane and ethyl acetate (3:1) with 2% acetic acid. The correct fractions were combined and evaporated in vacuo to afford an oil which was dissolved in heptane. Re-evaporation in vacuo afforded the title compound as a white powder (10.9 g, 45%).

TLC $R_f$ 0.16 (99% Ethyl acetate, 1% acetic acid).

Intermediate 7

(S)-2-Acetylsulfanyl-4-(2,5-dioxopyrrolidin-1-yl)butyric Acid

Intermediate 6 (10.5 g) was dissolved in methanol (53 mL) and cooled to 0° C. under nitrogen. To this solution was added potassium thioacetate (4.9 g) and the mixture warmed with stirring to ambient temperature, then stirred for 90 minutes. The solvent was then removed in vacuo and the residue resuspended in dichloromethane (200 mL) and water (30 mL). The aqueous layer was extracted with dichloromethane (3×200 mL) and the combined organic layers washed with brine (50 mL) and dried over magnesium sulfate. Filtration and evaporation afforded an oil which was mixed with diethyl ether (10 mL). After cooling to 2° C., crystals of the title compound were isolated by filtration (8.2 g, 80%).

MP 110–112° C.

Intermediate 8

Thioacetic Acid 1S-[1S-(2,2-Dimethyl-1S-methylcarbamoyl-propylcarbamoyl)-3-methylbutylcarbamoyl]-3-(2,5-dioxo-pyrrolidin-1-yl)propyl Ester Intermediate 7 (1.28 g) was dissolved in dichloromethane (32 mL) and cooled to 0° C. under nitrogen. To this solution was added 2-amino-4-methylpentanoic acid (2,2-dimethyl-1-methylcarbamoylpropyl)amide (1.33 g) rapidly followed by 1-hydroxybenzotriazole hydrate (0.667 g) and 1-(3-dimethylaminopropyl)-3-ethylcarbodiimide hydrochloride (1.14 g), after which the mixture was stirred at 0° C. for 45 minutes, then at ambient for 3.5 hours. The reaction was then diluted with dichloromethane (35 mL), washed with saturated aqueous sodium bicarbonate (20 mL), 1 M hydrochloric acid (20 mL) and water (30 mL), and dried over magnesium sulfate. Filtration and evaporation gave the crude title compound as a glassy solid (2.5 g, 100%).

TLC: $R_f$ 0.23 (Ethyl acetate).

EXAMPLE 1

2S-[4-(2,5-Dioxopyrrolidin-1-yl)-2S-mercaptobutyrylamino]-4-methylpentanoic Acid (2,2-Dimethyl-1S-methylcarbamoylpropyl)-amide Intermediate 8 (2.3 g) was dissolved in methanol (115 mL) and degassed. To this solution was added dithiothreitol (0.071 g). Degassing was performed again. Aqueous ammonia (3.0 mL) was added and the mixture stirred at ambient temperature for 45 minutes. The methanol was removed in vacuo to give an oil which was purified by column chromatography (ethyl acetate: methanol, 95:5). The correct fractions were combined and evaporated in vacuo at 40° C. to provide the title compound as a glassy solid (1.8 g, 86%). MP 81–84° C.

TLC $R_f$ 0.37 (Ethyl acetate:methanol, 95:5).

EXAMPLE 2

2S-[2S-Mercapto-4-(3,4,4-trimethyl-2,5-dioxoimidazolidin-1-yl) butyrylamino]-4-methylpentanoic Acid (2,2-Dimethyl-1S-methylcarbamoylpropyl)amide Was prepared as described for Example 6 in WO-A-9712902, by resolution of an intermediate involved in the synthesis or by separation of the distereoisomers of Example 6 in WO-A-9712902 by hplc.

Biological Data

The following Table reports results (in μM) from the assays described above, for the compounds of Examples 1 and 2, and also for the compound (Cpd. 3) of Example 52 of WO-A-9611209, i.e. (S)-N-[2-mercapto-5-phthalimido]pentanoyl-L-leucyl-(S)-tert-leucine N-methylamide.

| Assay | Cpd. 3 | Ex. 1 | Ex. 2 |
|---|---|---|---|
| Example A | | | |
| MMP-1 | 0.028 | 0.012 | 0.025 |
| MMP-8 | 0.009 | 0.010 | 0.010 |
| MMP-13 | 0.002 | 0.004 | 0.004 |
| MMP-2 | 0.015 | 0.130 | 0.041 |
| MMP-9 | 0.005 | 0.053 | 0.025 |
| MMP-3 | 0.179 | 0.381 | 0.157 |
| Example B | 10 | IA | IA |
| Example C | IA | IA | IA |
| Example D | IA | 38 | IA |
| Example E | IA | IA | IA |
| Example F | IA | IA | IA |

IA means no activity at the highest concentration tested, which was 50 or 100 μM.

We claim:

1. A compound selected from the group consisting of 2S-[4-(2,5-dioxopyrrolidin-1-yl)-2S-mercaptobutyrylamino]-4-methylpentanoic acid (2,2-dimethyl-1S-methylcarbamoylpropyl)amide and 2S-[2S-mercapto-4-(3,4,4-trimethyl-2,5-dioxolmidazolidin-1-yl)butyrylamino]-4-methylpentanoic acid (2,2-dimethyl-1S-methylcarbamoylpropyl)amide.

2. The compound according to claim 1, wherein the compound is 2S-[4-(2,5-dioxopyrrolidin-1-yl)-2S-mercaptobutyrylamino]-4-methylpentanoic acid (2,2-dimethyl-1S-methylcarbamoylpropyl)amide.

3. The compound according to claim 1, wherein the compound is 2S-[2S-mercapto-4-(3,4,4-trimethyl-2,5-dioxoimidazolidin-1-yl)butyrylamino]-4-methylpentanoic acid (2,2-dimethyl-1S-methylcarbamoylpropyl)amide.

* * * * *

UNITED STATES PATENT AND TRADEMARK OFFICE
CERTIFICATE OF CORRECTION

PATENT NO. : 6,818,622 B2
DATED : November 16, 2004
INVENTOR(S) : John Bird et al.

It is certified that error appears in the above-identified patent and that said Letters Patent is hereby corrected as shown below:

Column 8,
Line 15, "dioxolmidazolidin" should read -- dioxoimidazolidin --.

Signed and Sealed this

Nineteenth Day of April, 2005

JON W. DUDAS
*Director of the United States Patent and Trademark Office*